(12) United States Patent
Hirai

(10) Patent No.: US 12,036,215 B2
(45) Date of Patent: Jul. 16, 2024

(54) ANTITUMOR AGENT AND METHOD FOR TUMOR THERAPY

(71) Applicant: TAIHO PHARMACEUTICAL CO., LTD., Chiyoda-ku (JP)

(72) Inventor: Hiroshi Hirai, Tokyo (JP)

(73) Assignee: TAIHO PHARMACEUTICAL CO., LTD., Chiyoda-ku (JP)

( * ) Notice: Subject to any disclaimer, the term of this patent is extended or adjusted under 35 U.S.C. 154(b) by 838 days.

(21) Appl. No.: 17/059,376

(22) PCT Filed: May 28, 2019

(86) PCT No.: PCT/JP2019/020992
§ 371 (c)(1),
(2) Date: Nov. 27, 2020

(87) PCT Pub. No.: WO2019/230679
PCT Pub. Date: Dec. 5, 2019

(65) Prior Publication Data
US 2021/0236475 A1  Aug. 5, 2021

Related U.S. Application Data

(60) Provisional application No. 62/677,379, filed on May 29, 2018.

(51) Int. Cl.
*A61K 31/4545* (2006.01)
*A61K 31/337* (2006.01)
*A61P 35/00* (2006.01)

(52) U.S. Cl.
CPC ........ *A61K 31/4545* (2013.01); *A61K 31/337* (2013.01); *A61P 35/00* (2018.01)

(58) Field of Classification Search
CPC .... A61K 31/4545; A61K 31/337; A61P 35/00
USPC ...................................................... 514/318
See application file for complete search history.

(56) References Cited

U.S. PATENT DOCUMENTS

| 9,012,475 | B2 * | 4/2015 | Hirai | ..................... A61K 31/415 514/315 |
|---|---|---|---|---|
| 2015/0045342 | A1 | 2/2015 | Sugimoto et al. | |
| 2015/0065479 | A1 | 3/2015 | Hirai et al. | |
| 2016/0137628 | A1 | 3/2016 | Henry | |
| 2020/0087282 | A1 | 3/2020 | Mitsuya | |

FOREIGN PATENT DOCUMENTS

| JP | 2016-539942 A | 12/2016 |
|---|---|---|
| WO | WO 2013/129443 A1 | 9/2013 |
| WO | WO 2018/117267 A1 | 6/2018 |

OTHER PUBLICATIONS

Lapenna, S. et al., "Cell cycle kinases as therapeutic targets for cancer," Nature Reviews, Jul. 2009, vol. 8, pp. 547-566.
Mountzios, G. et al., "Aurora kinases as targets for cancer therapy," Cancer Treatment Reviews, 2008, vol. 34, pp. 175-182.
Yamada, H.Y. et al., "Spindle checkpoint function and cellular sensitivity to antimitotic drugs," Mol. Cancer Ther., Dec. 2006, vol. 5, No. 12, pp. 1-11.
Anand, S. et al., "Aurora-A amplification overrides the mitotic spindle assembly checkpoint, inducing resistance to taxol," Cancer Cell, Jan. 2003, vol. 3, pp. 51-62.
Hata, T. et al., "RNA Interference Targeting Aurora Kinase A Suppressed Tumor Growth and Enhances the Taxane Chemosensitivity in Human Pancreatic Cancer Cells," Cancer Research, Apr. 1, 2005, vol. 65, pp. 2899-2905 (9 total pages).
Kaestner, P. et al., "Determinants for the efficiency of anticancer drugs targeting either aurora-a or aurora-b kinases in human colon carcinoma cells," Molecular Cancer Therapeutics, Jul. 2009, vol. 8, pp. 2046-2056 (12 total pages).
Shimomura, T. et al., "MK-5108, a Highly Selective Aurora-A Kinase Inhibitor, Shows Antitumor Activity Alone in Combination with Docetaxel," Molecular Cancer Therapeutics, Jan. 12, 2010, vol. 9, No. 1, pp. 157-166 (11 total pages).
Journal of Thoracic Oncology, vol. 12, Issue 1, Supplement, 2017, pp. S261-S262, No. 1S, Abstracts, https://www.jto.org/article/S1556-0864(16)31495-2/pdf.
Ishihara, K. et al., "Abstract A269: A Selective Aurora A Inhibitor, TAS-119, Enhanced the antitumor activity of taxanes in an intermittent dosing schedule without affecting the neurotoxicity," Molecular Cancer Therapeutics, vol. 12, Issue 11, Nov. 2013, Supplement, total pp. 5.
International Search Report dated Aug. 27, 2019 in PCT/JP2019/020992 filed on May 28, 2019, 1 page.

* cited by examiner

*Primary Examiner* — Kristin A Vajda
(74) *Attorney, Agent, or Firm* — Oblon, McClelland, Maier & Neustadt, L.L.P.

(57) ABSTRACT

Provided is an effective method for using an orally administrable compound having an excellent Aurora A selective inhibitory effect, and a microtubule-targeting drug in combination. The present invention provides a method for treatment of malignant tumor by a combination of 1-(2,3-dichlorobenzoyl)-4-[5-fluoro-6-(5-methyl-1H-pyrazol-3-ylamino)pyridin-2-yl]methyl-4-piperidinecarboxylic acid (compound I) or a salt thereof and a microtubule-targeting drug, wherein the following administration schedule thereof is performed: one cycle involves 7 days; the microtubule-targeting drug is administered once; and the compound I or the salt thereof is administered for 3 consecutive days with cessation of the drug for remaining 4 days.

10 Claims, 3 Drawing Sheets

Fig. 2

Dose escalation treatment schedule

⬆ =Paclitaxel (IV)   ↑ =compound I (PO BID)

| week1 | | | | | | | week2 | | | | | | | week3 | | | | | | | week4 | | | | | | |
|---|---|---|---|---|---|---|---|---|---|---|---|---|---|---|---|---|---|---|---|---|---|---|---|---|---|---|
| 1 | 2 | 3 | 4 | 5 | 6 | 7 | 1 | 2 | 3 | 4 | 5 | 6 | 7 | 1 | 2 | 3 | 4 | 5 | 6 | 7 | 1 | 2 | 3 | 4 | 5 | 6 | 7 |
| ⬆↑↑↑ | | | | | | | ↑↑↑↑ | | | | | | | ⬆↑↑↑↑ | | | | | | | | | | | | | |

| Dose Level | compound I | | PTX | Pts# | DLT# | DLTs |
|---|---|---|---|---|---|---|
| | dosage | Days | dosage | | | |
| DL 1 | 25mg | D1,2,3,4 | 90mg/m² | 3 | 2 | G4 Neutropenia, G3 AST increased |
| DL 2 | 25mg | D2,3 | 70mg/m² | 3 | 0 | |
| DL 3 | 50mg | D2,3 | 70mg/m² | 4 | 0 | |
| DL 4 | 75mg | D2,3 | 70mg/m² | 3 | 0 | |
| DL 5 | 75mg | D2,3 | 80mg/m² | 3 | 0 | |
| DL 6 | 75mg | D2,3,4 | 80mg/m² | 7 | 0 | |
| DL 7 | 100mg | D2,3,4 | 80mg/m² | 3 | 2 | G3 Mucositis, G3 Diarrhea, G3 ALT increased | though an effect such as prolongation of a progression-free survival was observed.

ANTITUMOR AGENT AND METHOD FOR TUMOR THERAPY

This application is a national stage application of PCT/JP2019/020992, filed May 28, 2019, which claims priority to U.S. provisional application 62/677,379, filed May 29, 2018, the contents of both are incorporated herein their entirety.

TECHNICAL FIELD

The present invention relates to a method for tumor therapy by a combination of a microtubule-targeting drug and an Aurora A selective inhibitor, and further to a method for enhancing an antitumor effect of a microtubule-targeting drug using an Aurora A selective inhibitor. The present invention also relates to an antitumor agent and an antitumor-effect enhancer containing an Aurora A selective inhibitor which are administered according to a specific administration regimen.

BACKGROUND ART

Aurora A is a serine/threonine kinase. It is reported that Aurora A is involved in, e.g., formation and maturation of a centrosome, spindle kinetics and chromosome alignment in the mitotic phase (M phase) of the cell cycle, and regulates a process of mitotic division (Non Patent Literature 1). Up to present, overexpression and/or amplification of Aurora A have been confirmed in a wide variety of carcinomas (Non Patent Literature 2). Furthermore, inhibition of Aurora A kinase in a tumor cell induces arrest of mitotic division and apoptosis. Thus, Aurora A is one of important target molecules for cancer therapy.

Microtubule-targeting drugs such as taxane antitumor agents (taxanes) and vinca alkaloids have been widely used as cancer chemotherapeutic agents. However, due to refractoriness and resistance to these agents, sufficient therapeutic effects are not sometimes obtained. Thus, it is expected that an agent capable of enhancing the antitumor effect of a taxane antitumor agent can more effectively treat cancer. In the cytotoxicity reaction of a taxane antitumor agent, activation of a spindle assembly checkpoint in a cell cycle is required. In tumor cells reduced in this activity, sensitivity to a taxane antitumor agent decreases (Non Patent Literature 3). In addition, a cell line overexpressing Aurora A develops resistance to paclitaxel (Non Patent Literature 4). Thus, it has been reported that an effect of paclitaxel or docetaxel is enhanced by inhibiting Aurora A (Non Patent Literature 5).

In the meantime, Aurora B, which is a subtype of Aurora A, acts on the mitotic phase (M phase) of the cell cycle similarly to Aurora A. However, it has been reported that the inhibition of Aurora B reduces the activity of a spindle checkpoint (Non Patent Literature 6). Thus, there is a possibility that inhibition of Aurora B may attenuate the effect of a taxane antitumor agent. From the descriptions above, it is expected that combined use of an agent selectively inhibiting Aurora A kinase with a taxane antitumor agent can enhance the antitumor effect and provide a higher therapeutic effect.

MK-5108 is reported as an Aurora A selective inhibitor (Non Patent Literature 7). In Non Patent Literature 7, an antitumor effect was evaluated by administering MK-5108 and docetaxel to rats. Specifically, docetaxel was administered and then, 24 hours later, MK-5108 was orally administered twice per day for 2 days. As a result, it has been revealed that the tumor reduction effect of docetaxel is enhanced without exacerbating the side effect of docetaxel.

In a clinical trial using an Aurora A inhibitor and a taxane antitumor agent in combination, it has been reported that use of alisertib (MLN8237) and paclitaxel in combination is effective for small-cell lung cancer (SCLC) (Non Patent Literature 8). In this literature, an antitumor effect was measured by administering paclitaxel once per week, and also administering MLN8237 twice per day for 3 days, followed by cessation of the drugs for 4 days. This clinical trial was discontinued because serious adverse events such as neutropenia was found, though an effect such as prolongation of a progression-free survival was observed.

In the meantime, the present inventors' group has reported that a piperidine compound having a specific structure and a salt thereof have an Aurora A inhibitory effect (Patent Literature 1), and that hydrochloride of the piperidine compound exhibits the maximum antitumor effect by administration for 2 to 4 consecutive days in an in vivo study using rats (Non Patent Literature 9). The group has also reported the effect of an administration regimen in which the compound is used in combination with paclitaxel administered once per week, and administered twice per day for 4 days, followed by cessation of the drug for 3 days (Patent Literature 2). In the United States, clinical trials are ongoing in which 1-(2,3-dichlorobenzoyl)-4-[5-fluoro-6-(5-methyl-1H-pyrazol-3-ylamino)pyridin-2-yl]methyl-4-piperidinecarboxylic acid (hereinafter, referred to as compound I), which is one of the piperidine compound having a specific structure and the salt thereof, is administered alone or in combination with docetaxel or paclitaxel to a malignant tumor patient (clinicalTrials. gov. NCT02448589 and NCT02134067) Furthermore, crystals of hydrochloride of the compound have also been reported (Patent Literature 3).

CITATION LIST

Patent Literature

Patent Literature 1: International Publication No. WO 2013/129443
Patent Literature 2: U.S. Patent Publication No. 2015/0065479
Patent Literature 3: International Publication No. WO 2018/117267

Non Patent Literature

Non Patent Literature 1: Nat. Rev. Drug Discov., 8, p. 547-566 (2009)
Non Patent Literature 2: Cancer Treat. Rev., 34, p. 175-182 (2008)
Non Patent Literature 3: Mol. Cancer Ther., 5, p. 2963-2969 (2006)
Non Patent Literature 4: Cancer Cell, 3, p. 51-62 (2003)
Non Patent Literature 5: Cancer Res., 65, p. 2899-2905 (2005)
Non Patent Literature 6: Mol, Cancer Ther., 8, p. 2046-2056 (2009)
Non Patent Literature 7: Mol. Cancer Ther., 9, p. 157-166 (2010)
Non Patent Literature 8: Journal of Thoracic Oncology Volume 12, Issue 1, Supplement, Pages S261-S262 (2017)
Non Patent Literature 9: Molecular Targets and Cancer Therapeutics Volume 12, Issue 11, Supplement, Abstract A269 (2013)

SUMMARY OF INVENTION

Technical Problem

An object of the present invention is to provide a novel method for tumor therapy that exhibits a markedly excellent antitumor effect and has fewer side effects in a combination of an orally administrable Aurora A selective inhibitor and a microtubule-targeting drug (particularly, a tax an e antitumor agent).

Solution to Problem

The present inventor has found that in combined administration of a pyrimidine compound having a specific structure and a microtubule-targeting drug, administration according to specific doses and schedule particularly produces an excellent antitumor effect and antitumor enhancing effect, and completed the present invention.

Specifically, the present invention provides the following [1] to [58].

[1] An antitumor agent for combined administration with a microtubule-targeting drug to a malignant tumor patient, comprising 1-(2,3-dichlorobenzoyl)-4-[5-fluoro-6-(5-methyl-1H-pyrazol-3-ylamino)pyridin-2-yl]methyl-4-piperidinecarboxylic acid (compound I) or a salt thereof as an active ingredient, wherein the combined administration is performed according to the following schedule: one cycle involves 7 days or more; the compound I or a salt thereof is administered daily for 3 days and then not administered for 4 days in the cycle, and this operation is carried out once or more; and the microtubule-targeting drug is administered once per cycle.

[2] The antitumor agent according to [1], wherein the microtubule-targeting drug is a taxane antitumor agent.

[3] The antitumor agent according to [2], wherein the taxane antitumor agent is paclitaxel, and one cycle involves 7 days.

[4] The antitumor agent according to [3], wherein paclitaxel is administered at 70 to 80 mg/m$^2$/day.

[5] The antitumor agent according to [2], wherein the taxane antitumor agent is docetaxel, and one cycle involves 21 or 28 days.

[6] The antitumor agent according to [2], wherein the taxane antitumor agent is cabazitaxel, and one cycle involves 21 days.

[7] The antitumor agent according to any of [1] to [6], wherein the antitumor agent is administered at 50 to 150 mg/day in terms of an amount of the compound I.

[8] The antitumor agent according to any of [1] to [6], wherein the compound I is administered at 150 mg/day.

[9] The antitumor agent according to any of [1] to [8], wherein the compound I is in the form of hydrochloride.

[10] The antitumor agent according to any of [1] to [9], wherein the targeted malignant tumor is any of mesothelioma, blood cancer, head and neck cancer, rectal cancer, colon cancer, lung cancer, breast cancer, ovarian cancer, fallopian tube cancer, cervical cancer, prostate cancer, and brain tumor.

[11] An antitumor agent for treating a malignant tumor patient given a microtubule-targeting drug, comprising 1-(2,3-dichlorobenzoyl)-4-[5-fluoro-6-(5-methyl-1H-pyrazol-3-ylamino)pyridin-2-yl]methyl-4-piperidinecarboxylic acid (compound I) or a salt thereof as an active ingredient, wherein the antitumor agent is used according to the following schedule: one cycle involves 7 days or more; the compound I or a salt thereof is administered daily for 3 days and then not administered for 4 days in the cycle, and this operation is carried out once or more; and the microtubule-targeting drug is administered once per cycle.

[12] An antitumor-effect enhancer for enhancing an antitumor effect of a microtubule-targeting drug on a malignant tumor patient, comprising 1-(2,3-dichlorobenzoyl)-4-[5-fluoro-6-(5-methyl-1H-pyrazol-3-ylamino)pyridin-2-yl]methyl-4-piperidinecarboxylic acid (compound I) or a salt thereof as an active ingredient, wherein the antitumor-effect enhancer is used according to the following schedule: one cycle involves 7 days or more; the compound I or the salt thereof is administered daily for 3 days and not administered for remaining 4 days in the cycle, and this operation is carried out once or more; and the microtubule-targeting drug is administered once per cycle.

[13] A formulation or a pharmaceutical composition for treatment of tumor and/or enhancement of an antitumor effect of a microtubule-targeting drug, comprising the antitumor agent according to any of [1] to [11], or the antitumor-effect enhancer according to [12].

[14] A kit formulation comprising an antitumor agent comprising 1-(2,3-dichlorobenzoyl)-4-[5-fluoro-6-(5-methyl-1H-pyrazol-3-ylamino)pyridin-2-yl]methyl-4-piperidinecarboxylic acid (compound I) or a salt thereof, and an instruction for use, wherein the instruction for use states the following schedule: one cycle involves 7 days or more; the compound I or the salt thereof is administered daily for 3 days and then not administered for 4 days in the cycle, and this operation is carried out once or more; and the microtubule-targeting drug is administered once per cycle, for a malignant tumor patient.

[15] A method for treatment of malignant tumor, wherein the following schedule is performed: one cycle involves 7 days or more; 1-(2,3-dichlorobenzoyl)-4-[5-fluoro-6-(5-methyl-1H-pyrazol-3-ylamino)pyridin-2-yl]methyl-4-piperidinecarboxylic acid (compound I) or a salt thereof is administered daily for 3 days and then not administered for 4 days, and this operation is carried out once or more; and a microtubule-targeting drug is administered once per cycle, for a malignant tumor patient.

[16] A method for treatment for a malignant tumor patient given a microtubule-targeting drug, wherein the following schedule is performed: one cycle involves 7 days or more; 1-(2,3-dichlorobenzoyl)-4-[5-fluoro-6-(5-methyl-1H-pyrazol-3-ylamino)pyridin-2-yl]methyl-4-piperidinecarboxylic acid (compound 1) or a salt thereof is administered daily for 3 days and not administered for remaining 4 days, and this operation is carried out once or more; and the microtubule-targeting drug is administered once per cycle.

[17] A method for treatment for enhancing an antitumor effect of a microtubule-targeting drug on a malignant tumor patient, wherein the following schedule is performed: one cycle involves 7 days or more; 1-(2,3-dichlorobenzoyl)-4-[5-fluoro-6-(5-methyl-1H-pyrazol-3-ylamino)pyridin-2-yl]methyl-4-piperidinecarboxylic acid (compound I) or a salt thereof is administered daily for 3 days and not administered for remaining 4 days, and this operation is carried out once or more; and the microtubule-targeting drug is administered once per cycle.

[18] Use of an antitumor agent comprising 1-(2,3-dichlorobenzoyl)-4-[5-fluoro-6-(5-methyl-1H-pyrazol-3-ylamino)pyridin-2-yl]methyl-4-piperidinecarboxylic acid (compound I) or a salt thereof for treating a malignant tumor patient, wherein the antitumor agent is used according to the following schedule: one cycle involves 7 days or more; the compound I or the salt thereof is administered daily for 3 days and not administered for remaining 4 days, and this operation is carried out once or more; and the microtubule-targeting drug is administered once per cycle.

[19] Use of 1-(2,3-dichlorobenzoyl)-4-[5-fluoro-6-(5-methyl-1H-pyrazol-3-ylamino)pyridin-2-yl]methyl-4-piperidinecarboxylic acid (compound I) or a salt thereof for treating a malignant tumor patient given a microtubule-targeting drug, wherein the compound I or the salt thereof is used according to the following schedule: one cycle involves 7 days or more; the compound I or the salt thereof is administered daily for 3 days and not administered for remaining 4 days, and this operation is carried out once or more; and the microtubule-targeting drug is administered once per cycle.

[20] The use according to [19], wherein the microtubule-targeting drug is a taxane antitumor agent.

[21] The use according to [20], wherein the taxane antitumor agent is paclitaxel, and one cycle involves 7 days.

[22] The use according to [21], wherein paclitaxel is administered at 70 to 80 mg/m$^2$/day.

[23] The use according to [20], wherein the taxane antitumor agent is docetaxel, and one cycle involves 21 or 28 days.

[24] The use according to [20], wherein the taxane antitumor agent is cabazitaxel, and one cycle involves 21 days.

[25] The use according to any of to [24], wherein the compound I or the salt thereof is administered at 50 to 150 mg/day in terms of an amount of the compound I.

[26] The use according to any of to [24], wherein the compound I is administered at 150 mg/day.

[27] The use according to any of to [26], wherein the compound I is in the form of hydrochloride.

[28] The use according to any of to [27], wherein the malignant tumor to be targeted is any of mesothelioma, blood cancer, head and neck cancer, rectal cancer, colon cancer, lung cancer, breast cancer, ovarian cancer, fallopian tube cancer, cervical cancer, prostate cancer, and brain tumor.

[29] Use of an antitumor-effect enhancer comprising 1-(2,3-dichlorobenzoyl)-4-[5-fluoro-6-(5-methyl-1H-pyrazol-3-ylamino)pyridin-2-yl]methyl-4-piperidinecarboxylic acid (compound I) or a salt thereof for enhancing an antitumor effect of a microtubule-targeting drug on a malignant tumor patient, wherein the antitumor-effect enhancer is used according to the following schedule: one cycle involves 7 days or more; the compound I or the salt thereof is administered daily for 3 days and not administered for remaining 4 days, and this operation is carried out once or more; and the microtubule-targeting drug is administered once per cycle.

[30] Use of 1-(2,3-dichlorobenzoyl)-4-[5-fluoro-6-(5-methyl-1H-pyrazol-3-ylamino)pyridin-2-yl]methyl-4-piperidinecarboxylic acid (compound I) or a salt thereof for manufacturing an antitumor agent, the antitumor agent comprising the compound I or the salt thereof as an active ingredient and being used in combination with a microtubule-targeting drug, wherein the following administration schedule is performed: one cycle involves 7 days or more; the compound I or the salt thereof is administered daily for 3 days and not administered for remaining 4 days, and this operation is carried out once or more; and the microtubule-targeting drug is administered once per cycle.

[31] Use of 1-(2,3-dichlorobenzoyl)-4-[5-fluoro-6-(5-methyl-1H-pyrazol-3-ylamino)pyridin-2-yl]methyl-4-piperidinecarboxylic acid (compound I) or a salt thereof for manufacturing an antitumor agent for a malignant tumor patient given a microtubule-targeting drug, the antitumor agent comprising the compound I or the salt thereof as an active ingredient and being used in combination with the microtubule-targeting drug, wherein the following administration schedule is performed: one cycle involves 7 days or more; the compound I or the salt thereof is administered daily for 3 days and not administered for remaining 4 days; and the microtubule-targeting drug is administered once per cycle.

[32] Use of compound I or a salt thereof for manufacturing an antitumor-effect enhancer for a microtubule-targeting drug, the antitumor-effect enhancer comprising the compound I or the salt thereof as an active ingredient, wherein the following administration schedule is performed for enhancing the antitumor effect of the microtubule-targeting drug: one cycle involves 7 days or more; the compound I or the salt thereof is administered daily for 3 days and not administered for remaining 4 days, and this operation is carried out once or more; and the microtubule-targeting drug is administered once per cycle.

[33] An antitumor agent for combined administration with a microtubule-targeting drug to a malignant tumor patient, comprising 1-(2,3-dichlorobenzoyl)-4-[5-fluoro-6-(5-methyl-1H-pyrazol-3-ylamino)pyridin-2-yl]methyl-4-piperidinecarboxylic acid (compound I) or a salt thereof as an active ingredient, wherein the combined administration is performed according to the following schedule: one cycle involves 7 days; the compound I or the salt thereof is administered at 50 to 150 mg/day in terms of an amount of the compound I for 3 consecutive days with cessation of the drug for remaining 4 days; and the microtubule-targeting drug is administered at 70 to 90 mg/m$^2$/day in terms of an amount of the microtubule-targeting drug for 1 day among the 7 days.

[34] The antitumor agent according to [33], wherein the administration schedule is performed such that: one cycle involves 7 days; the compound I or the salt thereof is administered for 3 consecutive days from day 2 to day 4; and the microtubule-targeting drug is administered on day 1.

[35] The antitumor agent according to [34], wherein the administration schedule is set to 28 days and performed such that: the compound 1 or the salt thereof is administered for 3 consecutive days each from day 2 to day 4, from day 9 to day 11, and from day 16 to day 18; and the microtubule-targeting drug is administered on day 1, day 8, and day 15, followed by cessation of the drugs from day 22 to day 28.

[36] The antitumor agent according to any of to [35], wherein the microtubule-targeting drug is a taxane antitumor agent.

[37] The antitumor agent according to [36], wherein the taxane antitumor agent is paclitaxel.

[38] The antitumor agent according to any of to [37], wherein the microtubule-targeting drug is administered at 70 to 80 mg/m$^2$/day.

[39] The antitumor agent according to any of to [38], wherein the compound I is administered at 150 mg/day.

[40] The antitumor agent according to any of to [39], wherein the compound I is in the form of hydrochloride.

[41] The antitumor agent according to any of to [40], wherein the malignant tumor to be targeted is any of mesothelioma, blood cancer, head and neck cancer, rectal cancer, colon cancer, lung cancer, breast cancer, ovarian cancer, fallopian tube cancer, cervical cancer, prostate cancer, and brain tumor.

[42] An antitumor agent for treating a malignant tumor patient given a microtubule-targeting drug, comprising 1-(2,3-dichlorobenzoyl)-4-[5-fluoro-6-(5-methyl-1H-pyrazol-3-ylamino)pyridin-2-yl]methyl-4-piperidinecarboxylic acid (compound I) or a salt thereof as an active ingredient, wherein the antitumor agent is used according to the following schedule: one cycle involves 7 days; the compound I or the salt thereof is administered at 50 to 150 mg/day in terms of an amount of the compound I for 3 consecutive days with cessation of the drug for remaining 4 days; and the microtubule-targeting drug is administered at 70 to 90 mg/m$^2$/day in terms of an amount of the microtubule-targeting drug for 1 day among the 7 days.

[43] An antitumor-effect enhancer for enhancing an antitumor effect of a microtubule-targeting drug on a malignant tumor patient, comprising 1-(2,3-dichlorobenzoyl)-4-[5-fluoro-6-(5-methyl-1H-pyrazol-3-ylamino)pyridin-2-yl]methyl-4-piperidinecarboxylic acid (compound I) or a salt thereof as an active ingredient, wherein the antitumor-effect enhancer is used according to the following schedule: one cycle involves 7 days; the compound 1 or the salt thereof is administered at 50 to 150 mg/day in terms of an amount of the compound I for 3 consecutive days with cessation of the drug for remaining 4 days; and the microtubule-targeting drug is administered at 70 to 90 mg/m$^2$/day in terms of an amount of the microtubule-targeting drug for 1 day among the 7 days.

[44] A formulation or a pharmaceutical composition for treatment of tumor and/or enhancement of an antitumor effect of a microtubule-targeting drug, comprising the antitumor agent according to any of to [42], or the antitumor-effect enhancer according to [43].

[45] A kit formulation comprising an antitumor agent comprising 1-(2,3-dichlorobenzoyl)-4-[5-fluoro-6-(5-methyl-1H-pyrazol-3-ylamino)pyridin-2-yl]methyl-4-piperidinecarboxylic acid (compound I) or a salt thereof, and an instruction for use, wherein the instruction for use states the following schedule: one cycle involves 7 days; the compound I or the salt thereof is administered at 50 to 150 mg/day in terms of an amount of the compound I for 3 consecutive days with cessation of the drug for remaining 4 days; and the microtubule-targeting drug is administered at 70 to 90 mg/m$^2$/day in terms of an amount of the microtubule-targeting drug for 1 day among the 7 days, for a malignant tumor patient.

[46] A method for treatment of malignant tumor, wherein the following schedule is performed: one cycle involves 7 days; 1-(2,3-dichlorobenzoyl)-4-[5-fluoro-6-(5-methyl-1H-pyrazol-3-ylamino)pyridin-2-yl]methyl-4-piperidinecarboxylic acid (compound I) or a salt thereof is administered at 50 to 150 mg/day in terms of an amount of the compound I for 3 consecutive days with cessation of the drug for remaining 4 days; and a microtubule-targeting drug is administered at 70 to 90 mg/m$^2$/day in terms of an amount of the microtubule-targeting drug for 1 day among the 7 days, for a malignant tumor patient.

[47] The method for treatment according to [46], wherein the administration schedule is performed such that: one cycle involves 7 days; the compound I or the salt thereof is administered for 3 consecutive days from day 2 to day 4; and the microtubule-targeting drug is administered on day 1.

[48] The method for treatment according to [47], wherein the administration schedule is set to 28 days and performed such that: the compound I or the salt thereof is administered for 3 consecutive days each from day 2 to day 4, from day 9 to day 11, and from day 16 to day 18; and the microtubule-targeting drug is administered on day 1, day 8, and day 15, followed by cessation of the drugs from day 22 to day 28.

[49] The method for treatment according to any of to [48], wherein the microtubule-targeting drug is a taxane antitumor agent.

[50] The method for treatment according to [49], wherein the taxane antitumor agent is paclitaxel.

[51] The method for treatment according to any of to [50], wherein the microtubule-targeting drug is administered at 70 to 80 mg/m$^2$/day.

[52] The method for treatment according to any of to [50], wherein the compound I is administered at 150 mg/day.

[53] The method for treatment according to any of to [52], wherein the compound I is in the form of hydrochloride.

[54] The method for treatment according to any of to [53], wherein the malignant tumor to be targeted is any of mesothelioma, blood cancer, head and neck cancer, rectal cancer, colon cancer, lung cancer, breast cancer, ovarian cancer, fallopian tube cancer, cervical cancer, prostate cancer, and brain tumor.

[55] A method for treating a malignant tumor patient given a microtubule-targeting drug, wherein the following schedule is performed: one cycle involves 7 days; and the microtubule-targeting drug is administered at 70 to 90 mg/m$^2$/day in terms of an amount of the microtubule-targeting drug for 1 day among the 7 days, and then, 1-(2,3-dichlorobenzoyl)-4-[5-fluoro-6-(5-methyl-1H-pyrazol-3-ylamino)pyridin-2-yl]methyl-4-piperidinecarboxylic acid (compound I) or a salt thereof is administered at 50 to 150 mg/day in terms of an amount of the compound I for 3 consecutive days with cessation of the drug for remaining 4 days.

[56] A method for enhancing an antitumor effect of a microtubule-targeting drug on a malignant tumor patient, wherein the following schedule is performed: one cycle involves 7 days; the microtubule-targeting drug is administered at 70 to 90 mg/m$^2$/day in terms of an amount of the microtubule-targeting drug for 1 day among the 7 days; and 1-(2,3-dichlorobenzoyl)-4-[5-fluoro-6-(5-methyl-1H-pyrazol-3-ylamino)pyridin-2-yl]methyl-4-piperidinecarboxylic acid (compound I) or a salt thereof is administered at 50 to 150 mg/day in terms of an amount of the compound I for 3 consecutive days with cessation of the drug for remaining 4 days.

[57] Use of an antitumor agent consisting of 1-(2,3-dichlorobenzoyl)-4-[5-fluoro-6-(5-methyl-1H-pyrazol-3-ylamino)pyridin-2-yl]methyl-4-piperidinecarboxylic acid (compound I) or a salt thereof for treating a malignant tumor patient, wherein the antitumor agent is used according to the following schedule: one cycle involves 7 days; the compound I or the salt thereof is administered at 50 to 150 mg/day in terms of an amount of the compound I for 3 consecutive days with cessation of the drug for remaining 4 days; and the microtubule-targeting drug is separately administered at 70 to 90 mg/m$^2$/day in terms of an amount of the microtubule-targeting drug for 1 day among the 7 days.

[58] Use of an antitumor-effect enhancer comprising 1-(2,3-dichlorobenzoyl)-4-[5-fluoro-6-(5-methyl-1H-pyrazol-3-ylamino)pyridin-2-yl]methyl-4-piperidinecarboxylic acid (compound I) or a salt thereof for enhancing an antitumor effect of a microtubule-targeting drug on a malignant tumor patient, wherein the antitumor-effect enhancer is used according to the following schedule: one cycle involves 7 days; and the microtubule-targeting drug is administered at 70 to 90 mg/m$^2$/day in terms of an amount thereof for 1 day among the 7 days, and then, the compound I or the salt thereof is administered at 50 to 150 mg/day in terms of an amount of the compound I for 3 consecutive days with cessation of the drug for remaining 4 days.

The present specification encompasses the contents disclosed in U.S. Provisional Patent Application No. 62/677, 379 on which the priority of the present application is based.

Advantageous Effects of Invention

According to the administration schedule of the present invention, an excellent antitumor effect is obtained by the synergistic effects of a microtubule-targeting drug and compound 1 or a salt thereof, and a reductive effect on the volume of cancer targeted by treatment and enhancement of an antitumor effect is remarkable. Furthermore, according to the administration schedule of the present invention, the side effects of the microtubule-targeting drug and the compound I or the salt thereof can be minimized. Moreover, even for cancer that has become resistant due to administration of the microtubule-targeting drug, continuous administration of the microtubule-targeting drug can be expected by use in combination with the compound I or the salt thereof.

BRIEF DESCRIPTION OF DRAWINGS

FIG. 2 shows a dose escalation treatment schedule, efficacy and side effect by use of paclitaxel and compound I hydrochloride in combination for human cancer patients. One cycle involved 7 days. Paclitaxel was intravenously administered on day 1 each of weeks 1 to 3. Compound I hydrochloride was intraperitoneally administered twice per day from the same day as paclitaxel administration (DL1) or the day following paclitaxel administration (DL2 to DL7). Week 4 was set to a drug holiday (period of cessation of the drugs). Pts #: the number of patients given each dose level, DLT #: the number of patients observed to have dose-limiting toxicity. The arrows in the drawing illustrate administration of paclitaxel and compound I in DL6 and DL7.

DESCRIPTION OF EMBODIMENTS

Figure 1:
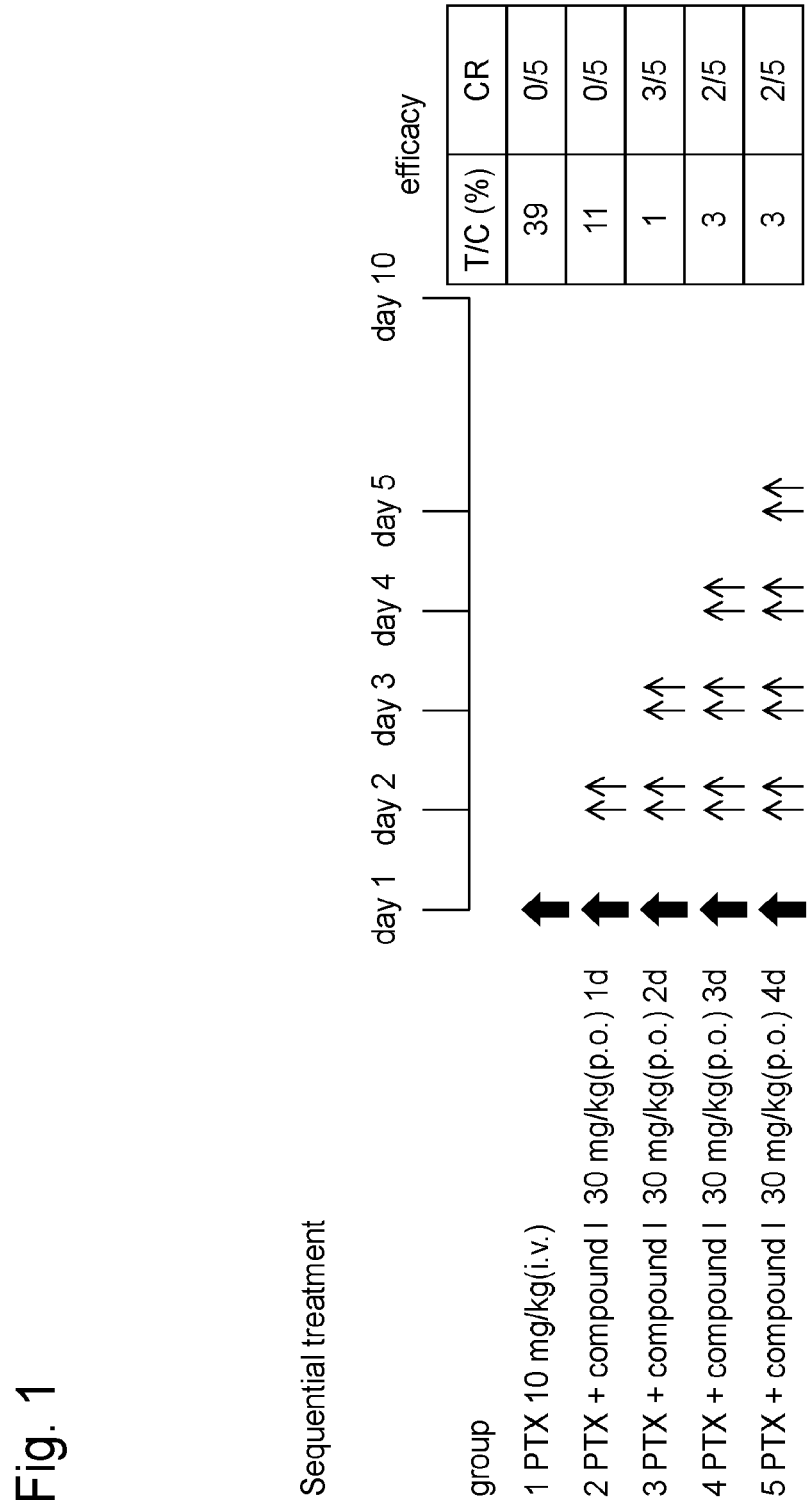
FIG. 1 shows a treatment schedule by sequential administration of paclitaxel (PTX) and compound I hydrochloride (compound I) for grafted tumor in nude rats to which human-derived uterus cancer cell line HeLa-luc cells were grafted, and its efficacy. To group 1, paclitaxel (10 mg/kg) alone was intravenously administered on day 1. To groups 2 to 5, paclitaxel was administered on day 1, and hydrochloride of compound I (30 mg/kg, based on free form) was orally administered twice per day for 1 day, 2 days, 3 days or 4 days (day 1 to day 5) from the following day. T/C represents a ratio (%) of an average relative tumor volume between a treatment group and a control group. CR represents the number of rats having complete remission among 5 rats.

The Aurora A selective inhibitor intended to be administered in combination with a microtubule-targeting drug in the present invention has the following structure, and has a chemical name of 1-(2,3-dichlorobenzoyl)-4-[5-fluoro-6-(5-methyl-1H-pyrazol-3-ylamino)pyridin-2-yl]methyl-4-piperidinecarboxylic acid (hereinafter, referred to as "compound I" in the present specification):

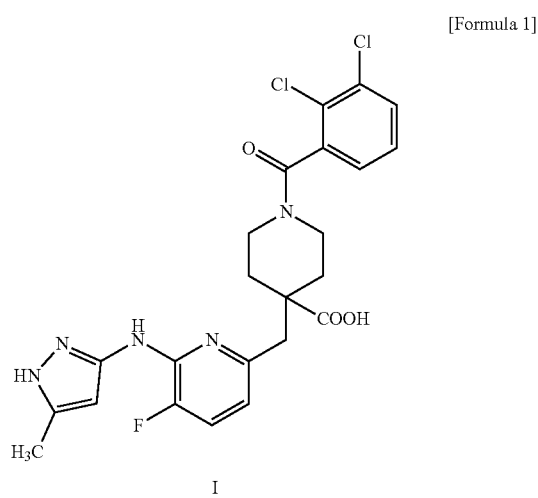

[Formula 1]

The compound I is excellent in Aurora A selective inhibitory activity. Use of the compound I or a salt thereof in combination with a microtubule-targeting drug has been found to bring about enhancement of an antitumor effect.

Thus, the present invention provides an antitumor agent for combined administration with a microtubule-targeting drug, comprising compound I having the structure described above or a salt thereof as an active ingredient, wherein the combined administration is performed according to the following schedule: one cycle involves 7 days or more; the compound I or the salt thereof is administered daily for 3 consecutive days and not administered for remaining 4 days, and this operation is carried out once or more; and the microtubule-targeting drug is administered once per cycle.

The present invention also provides an antitumor agent for treating a malignant tumor patient given a microtubule-targeting drug, comprising compound I or a salt thereof, wherein the antitumor agent is administered according to the schedule described above.

The present invention also provides an antitumor-effect enhancer for enhancing an antitumor effect of a microtubule-targeting drug on a malignant tumor patient, comprising compound I or a salt thereof, wherein the antitumor-effect enhancer is used according to the schedule described above.

The present invention further provides a formulation or a pharmaceutical composition for treatment of tumor and/or enhancement of an antitumor effect of a microtubule-targeting drug, comprising the antitumor agent or the antitumor-effect enhancer described above.

The present invention also provides a kit formulation comprising an antitumor agent comprising compound I or a salt thereof, and an instruction for use, the kit formulation being used according to the schedule described above for a malignant tumor patient, wherein the instruction for use describes a use method.

The present invention further provides a method for treatment of malignant tumor, wherein: one cycle involves 7 days or more; compound I or a salt thereof is administered daily for 3 days and not administered for remaining 4 days, and this operation is carried out once or more; and a microtubule-targeting drug is administered once per cycle, for a malignant tumor patient.

The present invention further provides a method for treating a malignant tumor patient given a microtubule-targeting drug, comprising administering the microtubule-targeting drug and compound I or a salt thereof according to the schedule described above.

The present invention further provides a method for enhancing an antitumor effect of a microtubule-targeting drug on a malignant tumor patient, comprising administering the microtubule-targeting drug and compound I or a salt thereof according to the schedule described above.

The present invention also provides use of an antitumor agent consisting of compound I or a salt thereof for treating a malignant tumor patient, wherein: one cycle involves 7 days or more; the compound I or the salt thereof is administered for 3 consecutive days and not administered for remaining 4 days, and this operation is carried out once or more; and a microtubule-targeting drug is separately administered once per cycle.

The present invention also provides use of compound I or a salt thereof for treating a malignant tumor patient given a microtubule-targeting drug, wherein the microtubule-targeting drug and the compound I or the salt thereof are used according to the schedule described above.

The present invention also provides use of an antitumor-effect enhancer comprising compound I or a salt thereof for enhancing an antitumor effect of a microtubule-targeting drug on a malignant tumor patient, wherein the microtubule-targeting drug and the compound I or the salt thereof are administered according to the schedule described above.

The present invention also provides use of compound I or a salt thereof for manufacturing an antitumor agent, the antitumor agent comprising the compound I or the salt thereof as an active ingredient and being used in combination with a microtubule-targeting drug, wherein the following administration schedule is performed: one cycle involves 7 days or more; the compound I or the salt thereof is administered daily for 3 days and not administered for remaining 4 days, and this operation is carried out once or more; and the microtubule-targeting drug is administered once per cycle.

The present invention also provides use of compound I or a salt thereof for manufacturing an antitumor agent for a malignant tumor patient given a microtubule-targeting drug, wherein the antitumor agent is used in combination with the microtubule-targeting drug according to the administration schedule described above.

The present invention also provides use of compound I or a salt thereof for manufacturing an antitumor-effect enhancer for a microtubule-targeting drug, wherein the microtubule-targeting drug and the compound I or the salt thereof are administered according to the administration schedule described above.

The compound I is one of piperidine compounds described in the International Publication No. WO 2013/129443 and U.S. Patent Publication No. 2015/0065479, and can be synthesized in accordance with a method described in the International Publication No. WO 2013/129443. This compound is excellent in oral absorbability and is important in terms of an effect of enhancing an antitumor effect of a microtubule-targeting drug.

The compound I is obtained as a white solid and may be present as crystals. The compound I can also be utilized as a pharmaceutically acceptable salt. Crystals of hydrochloride of the compound I can be synthesized according to the International Publication No. WO 2018/117267.

Examples of a pharmaceutically acceptable salt of the compound I include: salts with inorganic acids such as hydrochloric acid, hydrobromic acid, hydroiodic acid, sulfuric acid, nitric acid, and phosphoric acid; salts with organic acids such as formic acid, acetic acid, propionic acid, oxalic acid, malonic acid, succinic acid, ascorbic acid, isoascorbic acid, mandelic acid, fumaric acid, aspartic acid, maleic acid, lactic acid, malic acid, hippuric acid, glutaric acid, adipic acid, citric acid, tartaric acid, carbonic acid, picric acid, methanesulfonic acid (mesylic acid), p-toluenesulfonic acid (p-tosylic acid), and glutamic acid; and salts with alkali metals, alkaline earth metals, and other bases, for example, potassium salt, sodium salt, calcium salt, ammonium salt, methyl ammonium salt, and dimethyl ammonium salt.

Examples of the salt that is suitably used in the present invention can particularly include hydrochloride of the compound I. A salt having hydrochloric acid and the compound I at a molar ratio of 1:1 can be used as the hydrochloride of the compound I. This salt may be present in any form of single crystals, a mixture of two or more crystal polymorphs, an amorphous product, and a mixture thereof.

For example, the hydrochloride of the compound I or crystals thereof can be obtained, for example, by adding the compound I and hydrochloric acid to a certain solvent, and stirring the mixture for precipitation. More specifically, the hydrochloride of the compound I or crystals thereof can be obtained by a method comprising the steps of:

(1) adding 1-(2,3-dichlorobenzoyl)-4-[5-fluoro-6-(5-methyl-1H-pyrazol-3-ylamino)pyridin-2-yl]methyl-4-piperidinecarboxylic acid (compound I) and hydrochloric acid to a solvent; and (2) stirring the solvent obtained in the step (1) to precipitate hydrochloride of the compound I.

Examples of the solvent that can be used for producing the hydrochloride of the compound I or crystals thereof include water, $C_{1-6}$ alcohols (e.g., methanol, ethanol, n-propanol, and isopropanol), $C_{1-6}$ esters (e.g., methyl formate, ethyl formate, methyl acetate, ethyl acetate, isopropyl acetate, and butyl acetate), $C_{1-6}$ ketones (e.g., acetone, methyl ethyl ketone, methyl isopropyl ketone, methyl isobutyl ketone, and cyclohexanone), $C_{1-6}$ ethers (e.g., diethyl ether, t-butyl methyl ether, tetrahydrofuran, and 1,4-dioxane), hydrocarbons (e.g., n-hexane, n-pentane, n-heptane, cyclohexane, cyclopentane, and petroleum ether), aprotic polar solvents (e.g., acetonitrile, N-methyl-2-pyrrolidone, N,N-dimethylformamide, N,N-dimethylacetamide, and dimethyl sulfoxide), and mixed solvents thereof.

In the present invention, examples of the microtubule-targeting drug that can be administered in combination with the compound I or the salt thereof include microtubule-stabilizing drugs such as taxane antitumor agents and epothilone antitumor agents, and microtubule inhibitors such as vinca alkaloids, eribulin, and halichondrin B. The microtubule-targeting drug is preferably a microtubule-stabilizing drug, more preferably a taxane antitumor agent. Examples of the taxane antitumor agent include paclitaxel, docetaxel, and cabazitaxel. Paclitaxel or docetaxel is preferred, and paclitaxel is most preferred. Albumin-binding paclitaxel, docosahexaenoic acid-binding paclitaxel, polyglutamated paclitaxel, peptide-binding paclitaxel, or the like may be used as paclitaxel. Albumin-binding docetaxel or the like may be used as docetaxel. Examples of the epothilone antitumor agent include epothilone B and epothilone D. Examples of the vinca alkaloid include vinblastine and vincristine.

In the present invention, an antitumor agent other than the compound I or the salt thereof, or the microtubule-targeting drug may further be administered together with the microtubule-targeting drug that can be administered in combination with the compound I or the salt thereof.

The compound I or the salt thereof provides a synergistic excellent antitumor effect used in combination with the microtubule-targeting drug described above. The molar ratio of the compound I or the salt thereof in use per day is preferably 0.1 to 20 mol, more preferably 0.1 to 10 mol, still more preferably 1 to 5 mol, further preferably 1 to 4 mol, most preferably 1 to 3 mol, based on 1 mol of the microtubule-targeting drug. The weight ratio of the compound I in use per day is preferably 0.1 to 3, more preferably 0.5 to 2, further preferably 1 to 3, most preferably 1 to 1.5, based on 1 of the microtubule-targeting drug. In this context, in the case of using a complex-type agent such as albumin-binding paclitaxel, albumin-binding docetaxel, docosahexaenoic acid-binding paclitaxel, polyglutamated paclitaxel, or peptide-binding paclitaxel as the microtubule-targeting drug, the molar ratio and the weight ratio described above are values based on paclitaxel or docetaxel in the complex.

In the present invention, examples of the malignant tumor to be targeted by treatment and enhancement of an antitumor effect include epithelial cancers (respiratory organ cancers, digestive organ cancers, cancers of the reproductive system, cancers of the secretion system, etc.), sarcomas, tumors of the hematopoietic system (B cell lymphoma, chronic lymphatic leukemia, peripheral T cell lymphoma, myelodysplastic syndrome, acute myeloid leukemia, acute lymphatic leukemia, etc.), tumors of the central nervous system, tumors of the peripheral nervous system, and multiple myeloma. The targeted type of carcinoma is preferably an epithelial cancer or a tumor of the hematopoietic system, more preferably a respiratory organ cancer, a digestive organ cancer, a cancer of the reproductive system, or a tumor of the hematopoietic system.

The type of an organ in which tumor is developed is not particularly limited. Examples of the tumor include head and neck cancer such as parotid gland cancer, esophagus cancer, stomach cancer, duodenal cancer, colon cancer, rectal cancer, hepatocarcinoma, gallbladder or bile duct cancer, biliary cancer, pancreatic cancer, lung cancer, breast cancer, ovarian cancer, fallopian tube cancer, cervical cancer, endometrial cancer, kidney cancer, adrenal cancer, bladder cancer, prostate cancer, urothelial cancer, testicular cancer, bone or soft-tissue sarcoma, blood cancer, multiple myeloma, skin cancer, brain tumor, and mesothelioma. The tumor targeted by therapy is preferably mesothelioma, blood cancer, head and neck cancer, urothelial cancer, adrenal cancer, pancreatic cancer, hepatocellular carcinoma, parotid gland cancer, rectal cancer, colon cancer, gallbladder or bile duct cancer, lung cancer, breast cancer, ovarian cancer, fallopian tube cancer, cervical cancer, prostate cancer, and/or brain tumor, more preferably mesothelioma, blood cancer, head and neck cancer, rectal cancer, colon cancer, ovarian cancer, fallopian tube cancer, lung cancer, breast cancer, brain tumor and/or prostate cancer, particularly preferably head and neck cancer, ovarian cancer, and/or fallopian tube cancer.

The antitumor agent, the antitumor-effect enhancer, the method for tumor treatment and the method for enhancement of an antitumor effect of the present invention can also be applied to cancer resistant or refractory to an antitumor agent. In this context, the cancer resistant or refractory to an antitumor agent refers to cancer resistant or refractory to an agent such as a microtubule-targeting drug (taxane antitumor agents, epothilone anticancer agents, etc.), an alkylating agent, an antimetabolite, an antitumor antibiotic, a hormone-mimetic drug, a platinum-containing drug, a topoisomerase inhibitor, a cytokine, a molecular target therapeutic drug, or a non-specific immunostimulant, and includes cancer resistant or refractory to combined use of these agents. Cancer resistant to a microtubule-targeting drug is preferred, and cancer resistant to a taxane antitumor agent is more preferred. Cancer resistant to paclitaxel, docetaxel, or cabazitaxel is particularly preferred, and cancer resistant to paclitaxel is most preferred.

The number of administration per administration day according to the present invention is once or more per day, preferably once per day, for the microtubule-targeting drug. The number of administration per day of the compound I is once or more per day, preferably twice per day.

The administration schedule for treatment of tumor and enhancement of an antitumor effect found in the present invention is the following schedule: one cycle involves 7 days or more; the microtubule-targeting drug is administered once per cycle; and the compound I or the salt thereof is administered for 3 consecutive days and then not administered for 4 days. This schedule of "administered for X consecutive days and then not administered for Y days" can also be expressed in another way as "X on Y off". For example, the schedule of "administered for 3 consecutive days and then not administered for 4 days" can be expressed as 3 on 4 off, and the schedule of "administered for 2 consecutive days and then not administered for 5 days" can be expressed as 2 on 5 off. A drug holiday can be appropriately set between cycles. For example, 3 cycles can be performed, followed by cessation of the drug for 1 week, or 1 cycle can be performed, followed by cessation of the drug for 3 weeks. One cycle may be performed continuously once to three times or more, which can be appropriately selected in consideration of the type of cancer, symptoms of a cancer patient, etc.

The number of days in one cycle in the method for tumor treatment and the method for enhancement of an antitumor effect of the present invention is 7 to 28 days per cycle. When the microtubule-targeting drug is paclitaxel, one cycle preferably involves 7 days, 14 days, or 21 days, more preferably 7 days. When the microtubule-targeting drug is docetaxel, one cycle preferably involves 21 days or 28 days. When the microtubule-targeting drug is cabazitaxel, one cycle preferably involves 21 days.

As for the number of consecutive days of administration of the compound I or the salt thereof in one cycle, if the days for administration is short, enhancement of the antitumor effect will be insufficient. In contrast, if the days for administration is long, development of a side effect may be concerned, which is also undesirable in view of medical cost. It is preferred that: the number of consecutive days of administration of the compound I or the salt thereof in one cycle involving 7 days or more should be 3 days; and the compound I or the salt thereof should not be administered for remaining 4 days. The cycle may be performed continuously and repetitively, and a drug holiday may be appropriately set between cycles.

For the administration order of the microtubule-targeting drug and the compound I or the salt thereof in one cycle, in view of enhancement of an antitumor effect and suppression of a side effect, it is preferred that administration of the compound I or the salt thereof should be initiated on the same day as or 1 to 4 days after administration of the microtubule-targeting drug. It is more preferred that administration of the compound I or the salt thereof should be initiated on the same day as or 1 day after administration of the microtubule-targeting drug. It is most preferred that administration of the compound I or the salt thereof should be initiated 1 day after administration of the microtubule-targeting drug.

A more specific administration schedule according to the present invention in light of the number of consecutive days of administration of the compound I and the administration order thereof with the microtubule-targeting drug is preferably the following schedule: one cycle involves 7 days or more; the microtubule-targeting drug is administered once per cycle; and the compound I or the salt thereof is administered once or more per day for 3 consecutive days from the same day as or the day following administration of the microtubule-targeting drug and not administered for remaining 4 days. A drug holiday can be appropriately set between cycles and after the completion of cycle(s). In the case of initiating administration of the compound I or the salt thereof on the day following administration of the microtubule-targeting drug in continuous cycles, day 4 in a final period in which the compound I or the salt thereof is not administered is the same day as the first day of the next cycle.

A detailed administration schedule can be any of the following schedules:
 (i) one cycle involves 7 days; the microtubule-targeting drug is administered on day 1; administration of the compound I or the salt thereof is initiated on the same day as or the day following administration of the microtubule-targeting drug; and a period of consecutive days of administration of the compound I or the salt thereof is 3 days;
 (ii) a cycle of 7 days is carried out twice for 14 days; the microtubule-targeting drug is administered on day 1 and day 8; administration of the compound I or the salt thereof is initiated on the same day as or the day following administration of the microtubule-targeting drug; and a period of consecutive days of administration of the compound I or the salt thereof is 3 days for each cycle, and the compound I or the salt thereof is not administered for subsequent 4 days;
 (iii) a cycle of 7 days is carried out three times for 21 days; the microtubule-targeting drug is administered on day 1, day 8, and day 15; administration of the compound I or the salt thereof is initiated on the same day as or the day following administration of the microtubule-targeting drug; and a period of consecutive days of administration of the compound I or the salt thereof is 3 days for each cycle, and the compound I or the salt thereof is not administered for subsequent 4 days; and
 (iv) a cycle of 7 days is carried out three times in 28 days; the microtubule-targeting drug is administered on day 1, day 8, and day 15; administration of the compound I or the salt thereof is initiated on the same day as or the day following administration of the microtubule-targeting drug; and a period of consecutive days of administration of the compound I or the salt thereof is 3 days, and the compound I or the salt thereof is not administered for subsequent 4 days each for the 3 cycles, followed by a drug holiday for 7 days. The interval between cycles may further be extended so that a drug holiday can be appropriately set. The cycle may be performed further continuously and repetitively.

The administration schedule is more preferably performed such that: one cycle involves 7 days; the microtubule-targeting drug is administered once, on day 1, among 7 days, twice, on day 1 and day 8, among 14 days, or three times, on day 1, day 8, and day 15, among 21 days; the compound I or the salt thereof is administered twice or more per day for 3 consecutive days from day 2 among 7 days when the microtubule-targeting drug is administered once, each from day 2 and day 9 among 14 days when the microtubule-targeting drug is administered twice, or each from day 2, day 9, and day 16 over 21 days, which can be followed by a drug holiday for 7 days or longer after the completion of a cycle when the microtubule-targeting drug is administered three times. A drug holiday can be appropriately set after the completion of cycle(s).

In another embodiment, in one cycle, the microtubule-targeting drug is administered on day 1, and administration of the compound I or the salt thereof is initiated on the following day. In this case, any of the following administration schedules is performed:
 (i) one cycle involves 7 days; the microtubule-targeting drug is administered only on day 1; and the compound I or the salt thereof is administered for 3 consecutive days from day 2 and not administered for 4 days;
 (ii) one cycle involves 14 days; the microtubule-targeting drug is administered only on day 1; and the compound I or the salt thereof is administered for 3 consecutive days from day 2 and not administered for 4 days;
 (iii) one cycle involves 21 days; the microtubule-targeting drug is administered only on day 1; and the compound I or the salt thereof is administered for 3 consecutive days from day 2 and then not administered for 4 consecutive days; and this operation is carried out three times;
 (iv) one cycle involves 28 days; the microtubule-targeting drug is administered on day 1; and the compound I or the salt thereof is administered for 3 consecutive days from day 2 and then not administered for 4 consecutive days; and this operation is carried out four times; and
 (v) one cycle involves 7 days and is carried out three times, and a drug holiday may be appropriately set between cycles and after the completion of the cycles. Specifically, the microtubule-targeting drug is administered on day 1, day 8, and day 15; the compound I or the salt thereof is administered daily for 3 days from the day following administration of the microtubule-targeting drug and then not administered for 4 days, and this operation is carried out three times; and a drug holiday can be appropriately set after the completion of the cycles.

In this context, the administration route of the microtubule-targeting drug depends on the type of each agent, and can be, for example, intravenous injection, intraperitoneal injection, administration using a suppository, or oral administration, and is generally intravenous administration or intraperitoneal administration. On the other hand, the administration route of the compound I or the salt thereof is preferably oral administration.

The compound I or the salt thereof can be provided as a formulation or a pharmaceutical composition comprising the compound I or the salt thereof as an active ingredient. The microtubule-targeting drug or a salt thereof can also be provided as a formulation or a pharmaceutical composition comprising the microtubule-targeting drug or the salt thereof as an active ingredient. Also, the microtubule-targeting drug and the compound I or the salt thereof can be provided as a kit formulation comprising separate formulations each comprising the microtubule-targeting drug or the compound I or the salt thereof alone. The kit formulation may be, for example, a kit formulation comprising an antitumor agent comprising compound I or a salt thereof, and an instruction for use, wherein the instruction for use states that: the compound I or the salt thereof is administered once or more per day for 3 days to a cancer patient; and a microtubule-targeting drug is administered on day 1.

A dose (mg/body) to a subject is calculated as described below.

Dose (mg/body)=Dose (mg/m$^2$)×Body surface area (m$^2$)

The body surface area (BSA) can be determined according to, for example, DuBois's formula given below. The obtained value is rounded off to two decimal places.

BSA=([Body weight (kg)]$^{0.425}$×[Height (cm)]$^{0.725}$)×0.007184

The amount of the microtubule-targeting drug administered in each of the administration methods described above is 0.05 to 1000 mg/m$^2$/day for an oral agent, 0.01 to 500 mg/m$^2$/day for an injection, and 1 to 1000 mg/m$^2$/day for a suppository. The amount is more preferably 1 to 500 mg/m$^2$/day for an oral agent, 1 to 250 mg/m$^2$/day for an injection, and 1 to 500 mg/m$^2$/day for a suppository. The amount is further preferably 20 to 200 mg/m$^2$/day for an injection. However, the amount can be increased depending on symptoms of a patient, a dosage form thereof, etc.

The dose of the microtubule-targeting drug per administration day differs depending on the type of an agent, the type and the stage of cancer, etc. When the microtubule-targeting drug is, for example, paclitaxel, its dose per day is 1 to 200 mg/m$^2$/day based on an amount of paclitaxel. The dose is more preferably 50 to 100 mg/m$^2$/day, further preferably 70 to 90 mg/m$^2$/day, and most preferably 70 to 80 mg/m$^2$/day. The number of administration is preferably once per day. However, the dose and the number of administration can be changed depending on symptoms, body weight, age, sex, etc. of a patient.

When the microtubule-targeting drug is paclitaxel, the dose of albumin-binding paclitaxel administered per day is 0.1 to 500 mg/m$^2$/day, preferably 1 to 300 mg/m$^2$/day, and more preferably 40 to 300 mg/m$^2$/day, based on an amount of paclitaxel. The number of administration is preferably once per day. However, the dose and the number of administration can be changed depending on symptoms, body weight, age, sex, etc. of a patient.

When the microtubule-targeting drug is docetaxel, its dose per day is 0.1 to 500 mg/m$^2$/day, preferably 1 to 100 mg/m$^2$/day, and more preferably 50 to 100 mg/m$^2$/day. The number of administration is preferably once per day. However, the dose and the number of administration can be changed depending on symptoms, body weight, age, sex, etc. of a patient.

When the microtubule-targeting drug is cabazitaxel, its dose per day is 0.1 to 100 mg/m$^2$/day, and preferably 1 to 25 mg/m$^2$/day. The number of administration is preferably once per day. However, the dose and the number of administration can be changed depending on symptoms, body weight, age, sex, etc. of a patient.

The dose of the compound I or the salt thereof to be administered in the administration mode described above is 1 to 500 mg/day, more preferably 50 to 200 mg/day, particularly preferably 50 to 150 mg/day, most preferably 150 mg/day, based on a weight of the compound I. This daily dose is usually administered twice per day in divided portions, and may be appropriately administered once to three times in divided portions per day. The number of administration in one day is preferably twice per day.

However, the dose and the number of administration can be changed depending on symptoms, body weight, age, sex, etc. of a patient.

Various types of organic or inorganic carrier substances routinely used as materials for formulations are used as pharmaceutical carriers contained in the formulation (pharmaceutical composition) comprising the compound I or the salt thereof An excipient, a binder, a disintegrator, a lubricant, and a coloring agent can be blended in a solid formulation. A solubilizing agent, a suspending agent, a tonicity agent, a buffer, and a soothing agent can be blended in a liquid formulation. If necessary, additives for formulations such as a preservative, an antioxidant, a sweetening agent, and a stabilizing agent can be used.

In the case of preparing an oral solid formulation, first, an excipient is added to the compound I or the salt thereof, and if necessary, another excipient, a binder, a disintegrator, a lubricant, a coloring agent, a flavoring agent, and the like are added. Then, the mixture can be formed into tablets, coating tablets, granules, powders, capsules, and the like by a conventional method. In the case of preparing an injection, first, a pH regulator, a buffer, a stabilizing agent, a tonicity agent, a local anesthetic drug, and the like are added to the compound.

Examples of the animal species to which the compound I or the salt thereof can be administered include mammals. The mammal is preferably a mammal to be treated as well as a mammal generally used in animal experiments such as pharmacokinetics or drug efficacy tests. Specific examples thereof include humans, rats, mice, rabbits, and dogs. A human is preferred.

The number of days in one cycle in the method for tumor treatment and the method for enhancement of an antitumor effect of the present invention can be 7 to 28 days per cycle. For example, one cycle involves 7 days; the microtubule-targeting drug is administered once per week; and the compound I or the salt thereof is administered once or more per day for 3 consecutive days from the same day as or 1 to 4 days after administration of the microtubule-targeting drug. The administration for 3 consecutive days is continuation of administration once to three times per day for 3 days and is also referred to administration daily for 3 days. The cycle may be carried out, for example, three times, followed by a drug holiday, for example, for 7 days. The dose of the compound I or the salt thereof per day to be administered in the administration mode described above is usually 0.05 to 5000 mg/day for an adult (body weight: 50 kg), and the number of administration is once to three times per day. The dose of the microtubule-targeting drug per administration day differs depending on the type of an agent, the type and the stage of cancer, etc. and is preferably 0.1 to 300 mg/m$^2$/day, for example, for paclitaxel.

More preferably, as for the administration order of the microtubule-targeting drug and the compound I or the salt thereof in one cycle, administration of the compound I or the salt thereof may be initiated on the same day as or 1 day after administration of the microtubule-targeting drug. A specific administration schedule in the method for tumor treatment and the method for enhancement of an antitumor effect of the present invention may be any of the following schedules:

(i) one cycle involves 7 days; the microtubule-targeting drug is administered on day 1; and administration of the compound I or the salt thereof is initiated on the day of administration of the microtubule-targeting drug or the day following this administration day, and the compound I or the salt thereof is administered for 3 consecutive days;

(ii) one cycle involves 7 days; the microtubule-targeting drug is administered on day 1 and day 8; and administration of the compound I or the salt thereof is initiated on the day of administration of the microtubule-targeting drug or the day following this administration day, and the compound I or the salt thereof is administered for 3 consecutive days;

(iii) one cycle involves 7 days; the microtubule-targeting drug is administered on day 1, day 8, and day 15; and administration of the compound I or the salt thereof is initiated on the day of administration of the microtubule-targeting drug or the day following this administration day, and the compound I or the salt thereof is administered for 3 consecutive days; and (iv) one cycle involves 7 days; the microtubule-targeting drug is administered on day 1, day 8, and day 15; administration of the compound I or the salt thereof is initiated on the day of administration of the microtubule-targeting drug or the day following this administration day, and the compound I or the salt thereof is administered for 3 consecutive days; and a drug holiday can be appropriately set between cycles and after the completion of cycle(s).

The dose of the compound I or the salt thereof per administration day in the administration mode described above is 50 to 200 mg/day, and the number of administration is twice per day. The dose of the microtubule-targeting drug per administration day is 50 to 100 mg/m$^2$/day, for example, for paclitaxel.

Further preferably, as for the administration order of the microtubule-targeting drug and the compound I or the salt thereof in one cycle, the microtubule-targeting drug is administered on day 1, and administration of the compound I or the salt thereof may be initiated 1 day after administration of the microtubule-targeting drug. A specific administration schedule in the method for tumor treatment and the method for enhancement of an antitumor effect of the present invention can be performed such that: the microtubule-targeting drug is administered once on day 1 among 7 days of 1 cycle, each on day 1 and day 8 in continuation for 14 days of 2 cycles, or each on day 1, day 8, and day 15 in continuation for 21 days of 3 cycles; and the compound I or the salt thereof is administered twice per day for 3 consecutive days from day 2 among 7 days, each from day 2 and day 9 among 14 days, or each from day 2, day 9, and day 16 among 21 days. A drug holiday can be appropriately set between cycles and after the completion of cycle(s). The dose of the compound I or the salt thereof per administration day of an agent having the administration mode described above is 150 mg/day, and the number of administration is twice per day. The dose of the microtubule-targeting drug per administration day is 70 to 80 mg/m$^2$/day, for example, for paclitaxel.

In another embodiment, in one cycle, the microtubule-targeting drug is administered on day 1, and administration of the compound I or the salt thereof is initiated on the following day. In this case, any of the following administration schedules is performed:

(i) one cycle involves 7 days; the microtubule-targeting drug is administered only on day 1; and the compound I or the salt thereof is administered for 3 consecutive days from day 2 and not administered for 4 days;

(ii) one cycle involves 14 days; the microtubule-targeting drug is administered only on day 1; and the compound I or the salt thereof is administered for 3 consecutive days from day 2 and not administered for 4 days;

(iii) one cycle involves 21 days; the microtubule-targeting drug is administered only on day 1; and the compound I or the salt thereof is administered for 3 consecutive days from day 2 and then not administered for 4 consecutive days; and this operation is carried out three times;

(iv) one cycle involves 28 days; the microtubule-targeting drug is administered on day 1; and the compound I or the salt thereof is administered for 3 consecutive days from day 2 and then not administered for 4 consecutive days; and this operation is carried out four times; and (v) one cycle involves 7 days and is carried out three times, and a drug holiday may be appropriately set between cycles and after the completion of a cycle. Specifically, the microtubule-targeting drug is administered on day 1, day 8, and day 15; the compound I or the salt thereof is administered daily for 3 days from the day following administration of the microtubule-targeting drug and then not administered for 4 days, and this operation is carried out three times; and a drug holiday can be appropriately set after the completion of cycle(s). The dose of the compound I or the salt thereof per day to be administered in the administration mode described above is usually 50 to 200 mg/day in an adult (body weight: 50 kg), and the number of administration is twice per day. The dose of the microtubule-targeting drug per administration day is 50 to 100 mg/m$^2$/day, for example, for paclitaxel.

In the present specification, the numerical values mentioned about the doses of the microtubule-targeting drug and the compound I or the salt thereof, and the ratio between these agents, etc. are intended to include values within ranges having ±20% or ±10% variation of the described numerical values. Those skilled in the art should understand that a dose or a ratio within such a range is capable of bringing about an effect similar to that of the described dose or ratio.

EXAMPLES

Hereinafter, the use of compound I or a salt thereof and a microtubule-targeting drug in combination of the present invention will be described in more detail with reference to Examples and Reference Examples. However, the present invention is not limited by these examples.

Reference Example 1 Synthesis of Hydrochloride of Compound I

Compound I (1-(2,3-dichlorobenzoyl)-4-[5-fluoro-6-(5-methyl-1H-pyrazol-3-ylamino)pyridin-2-yl]methyl-4-piperidinecarboxylic acid, 250 mg) obtained by the method described in Patent Literature 1 was suspended in ethanol (2.0 mL). To the suspension, a 4 M solution of hydrochloric acid in ethyl acetate (0.18 mL) and ethyl acetate (2.8 mL) were added in order, and the mixture was stirred at 85° C. for 6 hours. The obtained suspension was cooled to room temperature. Then, a solid was collected by filtration and washed with ethyl acetate. The obtained solid was dried under reduced pressure at 100° C. to obtain hydrochloride of the compound I (190 mg) as crystals.

The NMR spectrum of the compound I obtained by the method described in Patent Literature 1 was as follows: $^1$H-NMR (DMSO-D$_6$) δ: 10.34 (2/2H, brs), 7.70-7.59 (4/2H, m), 7.46-7.37 (3/2H, m), 7.32-7.29 (1/2H, m), 6.78-6.73 (2/2H, m), 6.32 (1/2H, s), 6.30 (1/2H, s), 4.24-4.20 (2/2H, m), 3.25-3.21 (2/2H, m), 3.09-2.97 (8/2H, m), 2.31 (3/2H, s), 2.29 (3/2H, s), 2.05-2.00 (2/2H, m), 1.91-1.81 (2/2H, m), 1.68-1.52 (4/2H, m) was observed. The mass was ESI-MS m/z 506,508 (MH-h).

Reference Example 2 Study on Schedule of Combined Use of Compound I and Paclitaxel Human-derived uterus cancer cell line HeLa-luc (PerkinElmer, Inc.) cells transfected with luciferase gene were subcutaneously grafted at $1 \times 10^7$ cells to the right abdomens of nude rats (lineage: F344/NJcl-rnu/rnu, female, distributor: CLEA Japan, Inc.). When the volume of the grafted tumor reached approximately 200 mm³, the rats were divided into groups each consisting of 5 rats according to stratified randomization such that each group had almost the same tumor volume.

To group 1, paclitaxel (10 mg/kg) alone was intravenously administered on day 1. To groups 2 to 5, paclitaxel was administered and, on the next day, the hydrochloride of the compound I (30 mg/kg, based on free form) obtained in Reference Example 1 was orally administered twice per day for 1 day, 2 days, 3 days or 4 days (Sequential treatment; see FIG. 1).

The hydrochloride of the compound I was suspended or dissolved in 0.5% (w/v) hydroxypropyl methyl cellulose (I-IPMC) Paclitaxel was dissolved in Cremophor EL and anhydrous ethanol, then diluted by the addition of physiological saline so as to obtain a predetermined concentration, and put in use. To a control group, only vehicles, specifically, 0.5% (w/v) hydroxypropyl methyl cellulose (HPMC), Cremophor EL, and anhydrous ethanol, were administered.

The presence or absence of a therapeutic effect was determined by measuring the major axis and minor axis of tumor with time and calculating a tumor volume (TV), relative tumor volume (RTV) and T/C (%) value (average relative tumor volume ratio of the treatment group to the control group) on day 10 after initiation of administration, according to the following formulas.

Tumor volume (TV)={(Major axis)×(Minor axis)²}/2

Relative tumor volume on measurement day (n)
($RTV_n$)=$TV_n/TV_1$

T/C (%)={(Average $RTV_n$ of the treatment group)/(Average $RTV_n$ of the control group)}×100

$TV_1$ represents tumor volume at the start of administration.

Furthermore, an individual in which a tumor disappeared was defined as CR (complete remission/complete response), and the number of cases was obtained.

As a result, no CR cases were observed in groups 1 and 2, whereas the number of CR cases was 3 in group 3, 2 in group 4, and 2 in group 5. In all the groups, no serious toxicity such as death was observed, and a side effect was acceptable.

As is apparent from these results, in the sequential administration, CR cases were observed in the group with an administration period of the compound I of 2 or more days. This demonstrated that a higher antitumor effect can be expected by employing an administration period of the compound I of 2 or more days.

Example Study on Administration Schedule in Combined Administration Test with Paclitaxel Paclitaxel and compound I in the form of hydrochloride were administered to cancer patients and evaluated for safety and efficacy. This study was conducted targeting solid cancer patients for whom a standard treatment is not effective, or a treatment is not present. Cancers found to affect the patients included the carcinoma shown in FIG. 3 (urothelial cancer, adrenal cancer, pancreatic cancer, colon cancer, cervical cancer, bile duct cancer, hepatocellular carcinoma, prostate cancer, head and neck cancer, ovarian cancer, gallbladder cancer, non-small cell lung cancer, parotid gland cancer, breast cancer, and fallopian tube cancer). This study also corresponds to a phase 1 clinical dose escalation trial for mainly evaluating safety and determining a recommended dose (RD), that can be administered safely without a concerned side effect in a phase 1 clinical expansion cohort test to be performed on a carcinoma basis.

In addition to the evaluation of safety, a therapeutic effect on tumor was also evaluated, if possible. The therapeutic effect on tumor was determined as a tumor reduction effect by comprehensive evaluation of target lesions (lesions equal to or larger than a measurable size according to a slice width by CT, etc.) and non-target lesions (all lesions other than the target lesions) with reference to the RECIST evaluation method (Journal of the National Cancer Institute, 2000, Vol 92, No. 3, 205-216J). The dose of the compound I is a weight based on free form.

In this study, PR (partial response) refers to 30% or more decrease in the sum of the major axis of target lesions, compared to that before administration. PD (progressive disease) refers to 20% or more relative increase in the sum of the major axis of target lesions, compared to the smallest sum of the major axis recorded after the start of the study, 5 mm or more absolute increase in the sum of the major axis, or apparent exacerbation of existing non-target lesions or a new lesion. SD (stable disease) refers to insufficient tumor reduction to qualify for PR and insufficient increase to qualify for PD, without progression and exacerbation of tumor, compared to the smallest sum of the major axis recorded after the start of the study.

FIG. 2 shows the administration schedule and dose of compound I and the dose of paclitaxel in the phase 1 dose escalation trial. A weekly administration regimen was adopted to paclitaxel, in which paclitaxel was administered once per week for 3 weeks, followed by cessation of the drug for 1 week. This administration method is a standard paclitaxel administration regimen and is widely used in clinical practice. On the other hand, the compound I was administered twice per day for 2 or 3 or 4 days from the same day as paclitaxel administration or 1 day after paclitaxel administration; this regimen was performed for 3 weeks together with the weekly paclitaxel administration; and week 4 was set to cessation of the compound I, in accordance with the cessation of paclitaxel. Each administration schedule (dose level) was evaluated from results of administration to 2 to 7 patients.

For dose level 1 (DL1), paclitaxel was administered weekly at 90 mg/m²/day; and the compound I was administered at 25 mg/dose twice per day for 4 days from the same day as paclitaxel administration, which was continued for 3 weeks. As a result, dose-limiting toxicity (DLT) was observed in two out of three patients. The observed dose-limiting toxicity includes grade 4 neutropenia with fever followed by sepsis in the first case, and grade 3 elevation of an aspartate aminotransferase (AST) level in biochemical examination of blood in the second case. Thus, this dose level was determined to exceed the maximum tolerable dose.

Hence, for dose level 2, the dose of paclitaxel was decreased to 70 mg/m²/day; and the compound I administration regimen was initiated 1 day after paclitaxel administration, and the number of administration days was changed to 2 days. As a result, DLT was not observed in any of three cases, and this level was determined to be tolerable. Accordingly, for dose level 3 or larger, as shown in FIG. 2, the study was continued by a method of escalating the dose of paclitaxel, the amount of the compound I administered per dose, and the number of administration days of the compound I.

As a result, dose-limiting toxicity was observed in two out of three cases at dose level 7 (dose of paclitaxel: 80 mg/m$^2$/day, amount of compound I administered per dose: 100 mg, administered twice per day for 3 days from the day following paclitaxel administration). Grade 3 mucositis and diarrhea were observed in the first case, and grade 3 alanine aminotransferase (ALT) elevation in biochemical examination of blood was observed in the second case. Thus, dose level 7 was determined to exceed the maximum tolerable dose.

On the other hand, grade 3 or higher dose-limiting toxicity was not observed in any of seven cases in the regimen of dose level 6 (dose of paclitaxel: 80 mg/m$^2$/day, dose of compound I per administration: 75 mg, administered twice per day for 3 days from the day following paclitaxel administration). Thus, this level was confirmed to be most suitable as the maximally tolerated dose.

Figure 3:
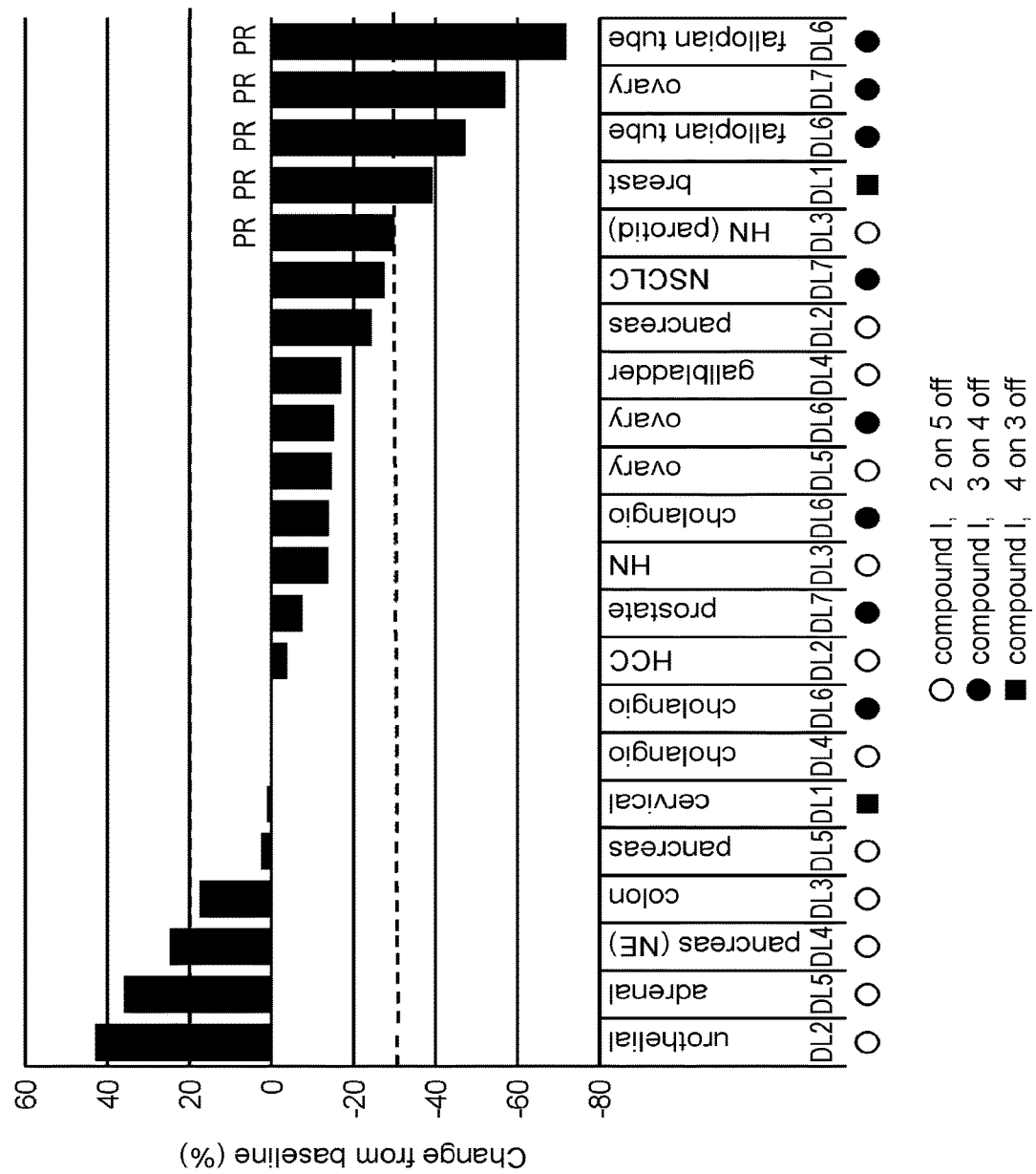
FIG. 3 shows a tumor reduction effect of compound I by a waterfall plot. The ordinate depicts a rate of change in tumor from the baseline, and the abscissa depicts results about each patient. Urothelial: urothelial cancer, adrenal: adrenal cancer, pancreas (NE: neuroendocrine): pancreatic cancer, colon: colon cancer, cervical: cervical cancer, cholangio: bile duct cancer, HCC: hepatocellular carcinoma, prostate: prostate cancer, HN: head and neck cancer, ovary: ovarian cancer, gallbladder: gallbladder cancer, NSCLC: non-small cell lung cancer, HN (parotid): parotid gland cancer, breast: breast cancer, fallopian tube: fallopian tube cancer. DL1 to DL7 represent dose levels performed for each patient. The open circles represent administration of compound I for 2 days in one cycle (DL2 to DL5). The filled circles represent administration of compound I for 3 days in one cycle (DL6 and DL7). The filled squares represent administration of compound I for 4 days in one cycle (DL1).

Among 24 patients with various types of carcinomas enrolled in this dose escalation trial, 22 cases for which a tumor reduction effect could be evaluated without inevaluable factors such as discontinuation of the trial were subjected to evaluation of a tumor reduction effect. As a result, as shown in FIG. 3, PR was observed in 5 patients having head and neck cancer (HN), breast cancer (breast), ovarian cancer (ovary), or fallopian tube cancer (fallopian tube; 2 cases).

When the tumor reduction effect is considered in relation to the administration schedule of the compound I, 8 out of 22 cases were given the compound I for 3 consecutive days, followed by cessation of the drug for 4 days (3 on 4 off) (dose levels 6 and 7), and 3 out of these 8 cases manifested PR (38%). On the other hand, only one out of 12 cases had PR (8.3%) in the administration schedule of the compound I, administered for 2 consecutive days, followed by cessation of the drug for 5 days (2 on 5 off). As for the number of cases in which a tumor reduction effect was observed without reaching PR, the tumor reduction effect was observed in 7 out of 8 patients (88%) in the 3 on 4 off schedule, whereas this effect was observed in only 6 out of 12 patients (50%) in the 2 on 5 off schedule.

In comparison between different numbers of administration days with an equal dose per day (dose levels 5 and 6), the tumor reduction effect was observed in 4 out of 5 cases (80%) in the 3 on 4 off schedule, whereas the tumor reduction effect was observed in only 1 out of 3 cases (33%) in the 2 on 5 off schedule. These results demonstrated that a 3 on 4 off schedule of compound I provides a marked tumor reduction effect as compared with 2 on 5 off schedule.

The clinical data on use of compound I and paclitaxel in combination demonstrated that, in view of tolerance, compound I administered in an amount of 25 mg per dose and at a total dose of 200 mg per week may produce toxicity, when the compound I is administered for 4 consecutive days. On the other hand, in administration of the compound I for 2 consecutive days, compound I administered in an amount of 75 mg per dose and at a total dose of 300 mg per week was found to be tolerable without the dose-limiting toxicity as described above. In administration of the compound I for 3 consecutive days, compound I administered in an amount of 75 mg per dose and at a total dose of 450 mg per week was found to be tolerable without the dose-limiting toxicity as described above.

In view of drug efficacy, unlike animal studies, the clinical trials demonstrated that administration of compound 1 for 3 or 4 consecutive days provides a stronger clinical effect than that for 2 days.

These results demonstrated that in consideration of balance between clinical antitumor effect and toxicity, administration of compound I according to a 3 on 4 off schedule is most suitable for an administration schedule of compound I and paclitaxel in combination.

As described above, a tumor reduction effect was obtained with suppressed serious side effect by adjusting the number of administration days and a dose. This result was unexpectable from the confirmation test on an antitumor effect in rats as shown in Reference Examples. For combined administration of compound I and paclitaxel to a human, it was revealed that a regimen in which paclitaxel is administered once per week while compound I or a salt thereof is administered twice per day for 3 consecutive days from the following day of paclitaxel administration, followed by cessation of the drug for 4 days exhibits an antitumor effect without serious side effects such as neutropenia.

All publications, patents and patent applications cited herein are incorporated herein by reference in their entirety.

The invention claimed is:

1. A method of administering a microtubule-targeting drug to a malignant tumor in a human patient in a treatment cycle comprising 7 days, comprising administering 1-(2,3-dichlorobenzoyl)-4-[5-fluoro-6-(5-methyl-1H-pyrazol-3-ylamino)pyridin-2-yl]methyl-4-piperidinecarboxylic acid or a salt thereof (compound I) as an active ingredient, wherein the combined administration is performed according to the following schedule: twice a day at 50 to 150 mg/day for 3 days and then not administered for 4 days in the cycle, and a taxane antitumor agent as the microtubule-targeting drug once per cycle.

2. The method of claim 1, wherein the taxane antitumor agent is paclitaxel, and one cycle involves 7 days.

3. The method of claim 2, wherein paclitaxel is administered at 70 to 80 mg/m$^2$/day.

4. The method of claim 1, wherein the taxane antitumor agent is docetaxel.

5. The method of claim 2, wherein the taxane antitumor agent is cabazitaxel.

6. The method of claim 1, wherein the compound I is administered at 150 mg/day.

7. The method of claim 1, wherein the compound I is in the form of hydrochloride salt.

8. The method of claim 1, wherein the targeted malignant tumor is any of mesothelioma, blood cancer, head and neck cancer, rectal cancer, colon cancer, lung cancer, breast cancer, ovarian cancer, fallopian tube cancer, cervical cancer, prostate cancer, and brain tumor.

9. A method of administering a microtubule-targeting drug to a malignant tumor in a human patient in a treatment cycle comprising 7 days, comprising administering 1-(2,3-dichlorobenzoyl)-4-[5-fluoro-6-(5-methyl-1H-pyrazol-3-ylamino)pyridin-2-yl]methyl-4-piperidinecarboxylic acid or a salt thereof (compound I) as an active ingredient, wherein the combined administration is performed according to the following schedule: twice a day at 50 to 150 mg/day on Days 2, 3, and 4 in the cycle, and a taxane antitumor agent as the microtubule-targeting drug on Day 1.

10. A method of administering a microtubule-targeting drug to a malignant tumor in a human patient in a treatment cycle comprising 28 days, comprising administering 1-(2,3-dichlorobenzoyl)-4-[15-fluoro-6-(5-methyl-1H-pyrazol-3-ylamino)pyridin-2-yl]methyl-4-piperidinecarboxylic acid or a salt thereof (compound I) as an active ingredient, wherein the combined administration is performed according to the following schedule: twice a day at 50 to 150 mg/day on Days 2, 3, 4, 9, 10, 11, 16, 17, and 18 in the cycle, and a taxane antitumor agent as the microtubule-targeting drug.

* * * * *